United States Patent
Marathe

(10) Patent No.: US 11,490,812 B2
(45) Date of Patent: Nov. 8, 2022

(54) SYSTEMS AND METHODS FOR MONITORING AND DETECTING SYMPTOMS OF INFECTIOUS CONDITIONS

(71) Applicant: Inseego Corp., San Diego, CA (US)

(72) Inventor: Amit Marathe, San Diego, CA (US)

(73) Assignee: Inseego Corp., San Diego, CA (US)

(*) Notice: Subject to any disclaimer, the term of this patent is extended or adjusted under 35 U.S.C. 154(b) by 221 days.

(21) Appl. No.: 16/942,629

(22) Filed: Jul. 29, 2020

(65) Prior Publication Data

US 2022/0031161 A1    Feb. 3, 2022

(51) Int. Cl.
   *A61B 5/117* (2016.01)
   *A61B 5/01* (2006.01)
   *A61B 5/00* (2006.01)

(52) U.S. Cl.
   CPC ............ *A61B 5/002* (2013.01); *A61B 5/0008* (2013.01); *A61B 5/0077* (2013.01); *A61B 5/117* (2013.01);
   (Continued)

(58) Field of Classification Search
   CPC .................................................... A61B 5/002
   See application file for complete search history.

(56) References Cited

U.S. PATENT DOCUMENTS

| | | |
|---|---|---|
| 10,362,769 B1 | 7/2019 | Kartoun |
| 2018/0262738 A1* | 9/2018 | Kapuria ............. H04N 5/23293 |

(Continued)

FOREIGN PATENT DOCUMENTS

| | | |
|---|---|---|
| CN | 103763790 A | 4/2014 |
| CN | 108695003 | 10/2018 |

(Continued)

OTHER PUBLICATIONS

Tracking Multiple People in a Multi-Camera Environment, https://www.epfl.ch/en/ link to embedded video reference: https://www.epfl.ch/labs/cvlab/research/research-surv/research-body-surv-index-php/, EPFL, Switzerland.

(Continued)

*Primary Examiner* — Joseph H Feild
*Assistant Examiner* — Pameshanand Mahase
(74) *Attorney, Agent, or Firm* — Sheppard, Mullin, Richter & Hampton LLP; Hector A. Agdeppa; Daniel N. Yanuzzi

(57) ABSTRACT

Systems and methods may include a first monitoring device positioned at a first location to monitor a monitored environment; and a second monitoring device positioned at a second location to monitor the monitored environment, wherein the first and second monitoring devices calibrate each other based on respective fiducial markers; wherein the first and second monitoring devices each comprise a processor and a memory coupled to the processor, the memory storing a plurality of instructions, which when executed by the processor, cause the processor to perform the operations of: detecting presence of the individual in the monitored environment; determining whether the condition of interest of the individual exceeds a determined threshold; based on the condition of interest of the individual exceeding the determined threshold, transmitting the condition of interest to a remote server to determine at least one of a social distancing breach and an identification of another person whom the individual contacted.

19 Claims, 5 Drawing Sheets

(52) U.S. Cl.
CPC ........ *A61B 5/48* (2013.01); *A61B 2562/0271* (2013.01)

(56) References Cited

U.S. PATENT DOCUMENTS

| | | | | |
|---|---|---|---|---|
| 2021/0391089 A1* | 12/2021 | Eswara | ................. | G16H 40/20 |
| 2021/0398691 A1* | 12/2021 | Dhamija | ................ | G16H 50/80 |
| 2022/0011293 A1* | 1/2022 | Hummer | ................ | G16H 10/40 |

FOREIGN PATENT DOCUMENTS

| | | |
|---|---|---|
| CN | 109378079 | 2/2019 |
| CN | 111339992 | 6/2020 |
| CN | 210895441 | 6/2020 |

OTHER PUBLICATIONS

The Smarter AI™ Bio Thermal Camera line-up, Any Connect, The Smarter AI™ Camera Platform, https://anyconnect.com/smarter-ai-bio-thermal-camera/.

* cited by examiner

US 11,490,812 B2

SYSTEMS AND METHODS FOR MONITORING AND DETECTING SYMPTOMS OF INFECTIOUS CONDITIONS

DESCRIPTION OF RELATED ART

Viral and bacterial infections can present a major health risk to the population. Various outbreaks over the years have spread across various parts of the globe causing death or serious illness. Examples of outbreaks of infectious diseases include smallpox (which was finally eradicated in the United States after more than 300 years thanks to a large vaccination initiative in 1972), yellow fever, typhoid Mary, H1N1, polio, measles, HIV, and COVID-19.

Infections that are airborne or that are spread through human contact can be difficult to contain. Once a human carrier is identified, they can be isolated to prevent them from infecting others. However, one of the challenges associated with preventing the spread of infection through human contact is identifying a carrier or spreader of the infectious disease early, during the contagious period. Persons may have early signs of illness and not be aware of the significance. For example, many infectious diseases often present with a fever, which if detected, could help to identify the infection. Unfortunately, fevers can go undetected and individuals may not appreciate the significance of a fever. Other signs and symptoms may also go undetected or unappreciated, frustrating early identification.

Once a carrier or spreader has been identified, it can be extremely helpful to identify others with whom that carrier has been in contact. This can help to warn those persons that they may need to seek treatment and also help to avoid further spread of the infection. Public health officials have long used this technique to limit the spread of infection and break the chain of transmission of infectious diseases. Challenges, however, can be with identifying the individuals themselves and understanding their movement and their chain of contacts.

BRIEF SUMMARY OF THE DISCLOSED TECHNOLOGY

According to various implementations of the disclosed technology systems and methods may be configured to provide a social distancing and temperature monitoring system they can also include contact tracing. Embodiments may be implemented to identify individuals in public or private areas who exhibit symptoms of an infectious disease. Once an individual has been identified, the system can be configured to alert the individual or health officials and to perform contact tracing to identify others with whom that identified individual has been or will be in contact.

In various embodiments, a system may include: a first monitoring device positioned at a first location to monitor a monitored environment; and a second monitoring device positioned at a second location to monitor the monitored environment, wherein the first and second monitoring devices calibrate each other based on respective fiducial markers; wherein the first and second monitoring devices each comprise a processor and a memory coupled to the processor, the memory storing a plurality of instructions, which when executed by the processor, cause the processor to perform the operations of: detecting presence of the individual in the monitored environment; determining whether the condition of interest of the individual exceeds a determined threshold; based on the condition of interest of the individual exceeding the determined threshold, transmitting the condition of interest to a remote server to determine at least one of a social distancing breach and an identification of another person whom the individual contacted. Embodiments may further include a communication interface to provide communication between the first and second monitoring device and the remote server. The communication interface may include a 5G communication terminal, such as a 5G hotspot or other 5G communication interface.

The first and second monitoring devices each may include a plurality of cameras, wherein the plurality of cameras capture images of individuals, and the captured images are used to determine locations of the individuals in the monitored environment, and further wherein the determined locations of individuals are used to determine whether the individuals are following determined social distance protocols.

The first and second monitoring devices each may further include a thermal sensor to detect information indicative of a temperature of individuals in the monitored environment.

The condition of interest of the individual may include a temperature of the individual, and wherein the operations may further include correlating temperature information collected by the thermal sensor with an individual detected in the monitoring environment to determine whether temperature information associated with that individual exceeds a threshold temperature.

The operations performed by the processor further may include identifying the individual and tracking the individual as the individual moves through the monitored environment. Identifying individual may include identifying the individual prior to the individual moving behind an occlusion and re-identifying the individual when the individual emerges from behind the occlusion.

The operations performed by the processor of the second monitoring device further may include, based on the second monitoring device detecting an individual in the monitoring environment, the second monitoring device instructing the first monitoring device to begin monitoring the monitored environment.

The condition of interest may include a distance between the individual and another individual in the environment, and wherein determining whether the condition of interest of the individual exceeds the threshold may include determining whether the individual is closer in distance to the other individual by less than a threshold amount.

Embodiments may further include the remote server, wherein the remote server is communicatively coupled to the first and second monitoring devices, the remote server receiving data from the first or second monitoring devices, the data indicative of the condition of interest regarding the individual present in the monitored environment.

In other embodiments, a system may include: a server; a plurality of monitoring stations, each monitoring station located at a physical location separate from the other monitoring stations, each monitoring station comprising a first monitoring device to monitor the location and a second monitoring device positioned to monitor the location from a different perspective from the first monitoring device; wherein the first and second monitoring devices each may include: a pair of cameras to capture images of the location; a thermal sensor to capture temperature information of individuals in the location; a processor; a memory coupled to the processor, the memory storing a plurality of instructions, which when executed by the processor, cause the processor to perform the operations of: detecting a presence of an individual in the monitored environment; correlating temperature information with image information to determine a temperature of the individual in the monitored environment; determining whether the temperature of the individual exceeds a determined threshold; and based on the condition of the temperature of the individual exceeding the determined threshold, transmitting the information to a remote server to determine, based on information from other monitoring stations, other locations visited by the individual and other individuals contacted by the individual.

The server may be configured to receive time stamped information from the plurality of monitoring stations relating to the individual in a plurality of the monitored environments, the information including temperature and location of the individual, and the server is configured to analyze image information of the scene from multiple angles to generate an inference regarding social distancing of the individual in the plurality of monitored environments. The server may be further configured to determine whether the individual made contact with other individuals in any of the plurality of monitored environments without following social distancing protocols.

The server may be further configured to identify another individual with whom the individual made contact without following social distance protocols and to generate an alert to the other individual informing the other individual of the contact.

The server may be further configured to identify physical locations visited by the individual and to generate an alert to the identified physical locations or to other individuals who also visited the identified physical locations.

The operations performed by the processor may further include identifying the individual and tracking the individual as the individual moves through the monitored environment.

Tracking the individual further may include identifying the individual prior to the individual moving behind an occlusion and re-identifying the individual when the individual emerges from behind the occlusion.

The operations performed by the processor of the second monitoring device further may include, based on the second monitoring device detecting an individual in the monitoring environment, the second monitoring device instructing the first monitoring device to begin monitoring the monitored environment.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

The figures are not exhaustive and do not limit the disclosure or the disclosed embodiments to the precise form disclosed.

DETAILED DESCRIPTION OF THE EMBODIMENTS

According to various implementations of the disclosed technology systems and methods may be configured to provide a social distancing and temperature monitoring system they can also include contact tracing. Embodiments may be implemented to identify individuals in public or private areas who exhibit symptoms of an infectious disease. Once an individual has been identified, the system can be configured to alert the individual or health officials and to perform contact tracing to identify others with whom that identified individual has been or will be in contact. In situations in which an individual is diagnosed a posteriori, stored data can be analyzed to determine who that individual may have come in close contact with in order to trace the spread.

Implementations may include a plurality of image sensors (e.g., cameras) and thermal sensors to collect information about individuals within their respective fields of view. A wired or wireless communication interface, such as a 5G wireless interface, can be included to exchange information about individuals in their symptoms with a server and to alert the individual or appropriate $3^{rd}$ parties regarding the detected symptoms. Artificial intelligence (AI) or other algorithms can be used to detect symptoms (e.g., a temperature above threshold) and identify instances of persons not following applicable social distancing protocols.

Figure 1:
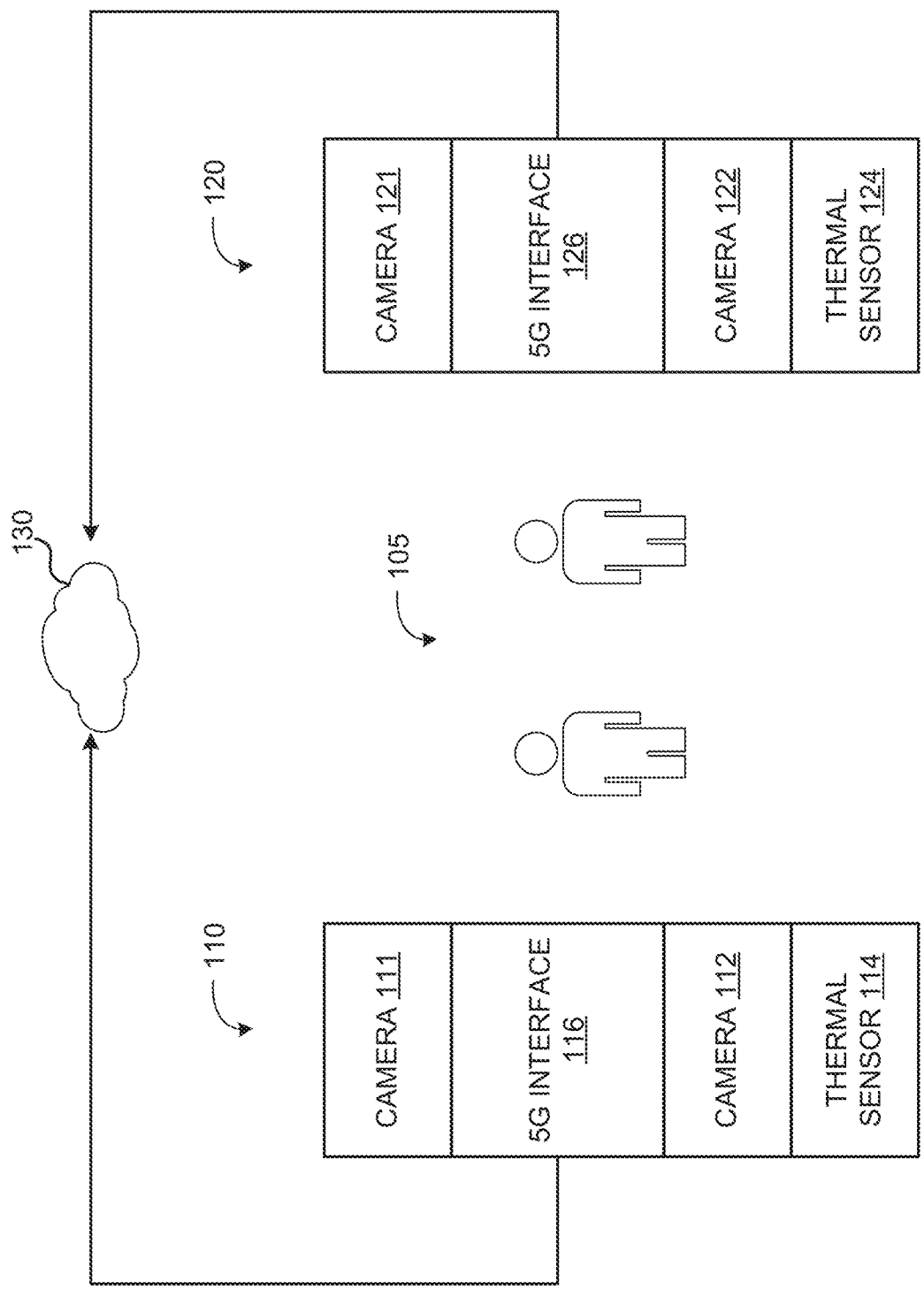
FIG. 1 illustrates an example system that can be used for identification of potential issues relating to the spread of infectious disease in accordance with various embodiments.

FIG. 1 illustrates an example system that can be used for identification of potential issues relating to the spread of infectious disease in accordance with various embodiments. This example includes two monitoring devices implemented as detection modules 110 and 120. These two monitoring devices are configured to monitor the same environment in which two individuals 105 are situated. In other implementations, there can be a different quantity of detection modules 110, 120. In this example, detection modules 110, 120 are similarly configured, each including a pair of cameras 111, 112 and 121, 122, a thermal sensor 114, 124, and a communication interface, which in the illustrated example includes a 5G hotspot 116, 126. Although not illustrated, each detection module 110, 120 may also include a fiducial marking that can be used by the other detection module, or other detection modules, for calibration and registration. Accordingly, the cameras of detection module 110 may use the fiducial markings of detection module 120 for calibration, and the cameras of detection module 120 may use a fiducial markings of detection module 110 for their calibration.

Detection modules 110 and 120 may be similarly configured as may other detection modules within a detection system. Accordingly, for ease of discussion, details of detection module 110 are now described with the understanding that the same or similar details may be applied to other detection modules in the system, including detection module 120.

Cameras 111, 112 may include, for example, visible light cameras, infrared cameras, ultrasound cameras, and other cameras configured to capture still or video images and produce an array of pixels or other image elements. Cameras may include image sensors that may be made up of an array of pixels. For visible light cameras, incident light may be focused through a lens or other optics onto the image sensor array. The image sensor array converts the optical energy incident on the pixels into electrical signals that can be processed to form an image. Image sensors may include, for example, Charge-Coupled Device (CCD), Complementary Metal Oxide Semiconductor (CMOS), and other image sensors.

Cameras 111, 112 in detection module 110 can be configured to provide a stereoptic view of the scene, including a view of one or more individuals 105 within the scene. This can provide a view of the same scene from two different perspectives (e.g., to the extent of field-of-view overlap). This can be used provide information for 3D depth perception to identify not only the position of objects in two dimension, but also the depth or distance to the objects. Although to cameras 111, 112 are shown for detection module 110, a different quantity of cameras may be provided. Multiple cameras may also be useful to compensate for blind spots that might be present in the scene. Cameras 111, 112 may be implemented with electronic or mechanical pan, tilt and zoom features.

Thermal sensor 114 may be used to capture a thermal signature of the scene. Information in the thermal signature may be used to, for example, measure the temperatures of different objects and individuals in the scene. In the case of individuals, surface temperature, such as the temperature of the skin on the face of an individual, may be used to determine internal body temperature. If the determined temperature is above the threshold, this can indicate that an individual has a symptom of an infectious disease. Thermal sensor 114 may be implemented as a thermographic or infrared camera or other thermal measurement system. In some applications, thermal sensor 114 may be implemented as a smart sensor that integrates one or more functions such as sensing, signal extraction, processing and comprehension into thermal sensor 114. Implementations may use any of a number of thermal detectors such as, for example infrared detectors (cooled or uncooled), including bolometers. Although one thermal sensor 114 is shown for detection module 110, the detection modules may include more than one thermal sensor. Thermal sensor 114 may also include mechanical or electronic pan, tilt and zoom features.

In the illustrated example, the communication interface is implemented as a 5G hotspot 116. 5G hotspot 116 can connect to a 5G tower were available, or may be configured to step down to 4G if a 4G signal is available instead. This ability can be provided to ensure that the system can maintain connectivity during deployment. Other wireless or wired communication interfaces can be provided in addition to or instead of 5G hotspot 126. For example, detection module 110 can include another 5G communications interface such as, for example, a 5G CPE or other 5G communication interface. As another example, detection module 110 can include a hardwired ethernet communication interface and ethernet port to allow the system to be hardwired into a communication network. As yet another example, detection module 110 can include Wi-Fi, Bluetooth, 3G, 4G or other wireless connectivity. As a further example, the communication interface can be include a proprietary or other non-standards-based communication interface.

The communication interface (e.g., 5G hotspot 116) can be used to communicate with a central server or other processing capability via a network 130 to allow data from multiple detection modules to be analyzed. Network 130 can be implemented as a wired or wireless communication network, or combination thereof, to facilitate data capture and sharing from among multiple detection modules. Embodiments may use a dedicated network or dedicated network slice along with data encryption to enhance data security and privacy for the information gathered and communicated.

As noted above, although not illustrated, detection module 110 can include a fiducial pattern marker or markers that can aid with system calibration of other detection modules (e.g., detection module 120 or others) that can view the fiducial pattern. The fiducial markers can provide anchors for location, orientation and scale. Given that the position of the fiducial marker on a detection module can be known, the fiducial marker can provide a calibration target to calibrate the cameras. These can be useful for finding intrinsic camera parameters such as, for example, focal length, scale factor, radial distortion, among others. These may also be useful for finding extrinsic parameters such as, for example, camera pose. The fiducial markers may be beneficial in that they can provide a way for the detection modules in a location to cross calibrate with one another. Accordingly, calibration of the cameras of one detection module can be based on fiducial markers of the cameras in the other detection module, and vice versa. This can provide a contained, ready solution for camera calibration without requiring external instrumentalities to be provided for the camera calibration.

In operation, cameras 111, 112 can capture a scene within their respective fields of view. The scene may include one or more individuals 105 as well as other objects. The system can be configured to identify individuals as persons. In some configurations, the system can be further configured to recognize the identity of identified individuals such as, for example, through facial recognition or other recognition techniques. In situations in which the identity of an identified individual is recognized, other information about that individual can be correlated to that individual including, for example, temperature measurements, location information (e.g., from various different detection modules that may capture images of the individual) contact information, and so on.

In situations in which facial recognition or other techniques are not available to determine the personal identity of an individual, other information may be gathered and used to uniquely or somewhat uniquely identify the person for data correlation purposes. For example, the system may use characteristics of the detected feature set to assign an identity to an individual such that that individuals movements can be tracked. These characteristics may include, for example, facial features height, build, a style, attire, and so on. Thus, although a personal identity of the individual might not be determined, individuals may still be uniquely tracked through the system using these identified characteristics. For example, the system can be configured to evaluate the characteristics and look for matches in the characteristics. A correlation of characteristics above a threshold can indicate a match for the individual. This can be useful, for example, to track an individual as they move about within the scene, even if they move behind and occlusion temporarily. This can also be useful to track an individual as they move from a current scene into a different scene monitored by different detection modules.

Thermal sensor 114 can capture temperature information for the scene. The temperature information can be correlated with image information captured from cameras 111, 112 to associate detected temperatures with their corresponding individuals. As noted above, temperature information can be processed to predict or approximate internal body temperature, and this information can be used to identify potential symptoms of disease or illness.

Information gathered from cameras 111, 112 and thermal sensor 114, as well as other information that may be gathered from other sensors, can be processed to determine useful information. This information may include, for example, body temperature predictions for individuals, social distancing of individuals, contacts made by individuals, locations visited by individuals, and so on. Locally gathered information may be processed locally at the detection module or may be sent to a central server (localized or cloud-based) for processing, or a combination of the foregoing. Information can also be shared among various detection modules for shared processing at the modules. Accordingly, embodiments can be implemented to include one or more processors that can be configured to perform edge computations from the camera and thermal sensor data, and to provide video and sensor data analysis on a cloud or other remote server platform.

Detection modules 110, 120 may also include clocks or a source of external timing information so that data can be timestamped and synchronized with data from other systems. This can allow internal and external synchronization of data sources to facilitate correlation of data from amongst multiple sensors within a detection module and across multiple detection modules. As noted above, although there are two detection modules 110, 120 illustrated in the example of FIG. 1, embodiments may be implemented with other quantities of detection modules. Including multiple detection modules allows redundancy of data, additional coverage of blind spots or other occlusion areas, and improve accuracy due to multiple measurements from different angles. Accordingly, various embodiments may include two or more detection modules at a single location.

Figure 2:
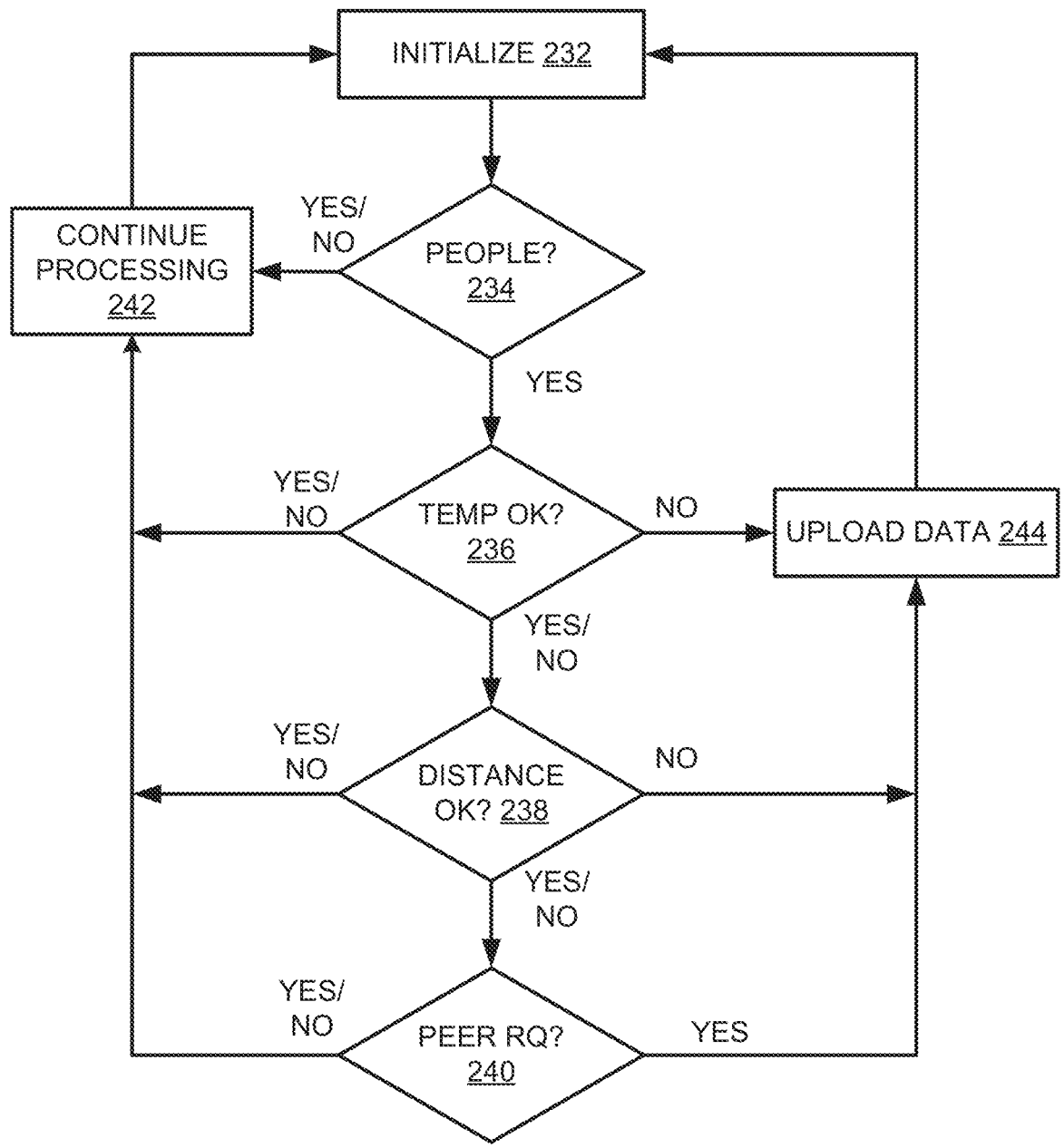
FIG. 2 illustrates an example concept of operations of a detection monitoring system in accordance with various embodiments.

FIG. 2 illustrates an example concept of operations of a detection and monitoring system in accordance with various embodiments. Particularly, this diagram illustrates an example of monitoring a plurality of individuals (e.g., individuals 105) in a scene for symptoms of infection (e.g., elevated temperature) and social distancing, or other condition of interest. Referring now to FIG. 2, at operation 232 the system is initialized, system initialization may include, for example, camera calibration. As noted above, camera calibration can be made or updated in situ using fiducial patterns within the field of view of the cameras. Initialization can be done at the time of installation, and can be repeated in whole or in part post installation. For example, dynamic camera calibration can take place at various times throughout the lifetime of the system.

Once initialized, the system monitors the data. At operation 234, the system analyzes data captured from the scene to determine whether there are any people in the scene. This can be accomplished, for example, using computer vision, motion detection or other techniques. Data such as, for example, image data captured from the cameras, temperature data from the thermal sensor, motion data captured from ultrasonic or other motion sensors, and so on, can be useful in this determination. An AI engine or other algorithm can be used to make a detection. This detection can be performed locally at the detection module 110, or remotely. If no individuals are detected in the scene, the system continues processing data from the scene is illustrated at operation 242. In some implementations, even if no people are detected, this information can be uploaded as well.

When individuals are detected at the scene, at operation 236 system evaluates temperature information of the individuals to determine whether one or more of the individuals has a temperature that is greater than a determine threshold. This can be determined based on external temperature (e.g., skin temperature) or based on a prediction of internal body temperature based on skin temperature. Embodiments may be configured to factor in environmental conditions when setting the threshold temperature measurement, as prolonged exposure to extreme environmental temperature conditions such as extreme heat or extreme cold can materially affect skin temperature. If the temperature of an individual is above threshold, the temperature data along with other data is uploaded for processing at operation 244. In embodiments where processing occurs at the cloud or other central processing facility, the data is uploaded to the processing facility. This can include identification information as well as temperature information. The upload can take place wired or wirelessly such as, for example, through a 5G mobile hotspot.

If the measured temperature of the individual is not indicative of an issue, (e.g., not above threshold), at operation 238 the system performs measurements to determine whether social distancing protocols are being observed. In some embodiments, this can be performed regardless of whether the measured temperature is within normal balance. The system can use information from the cameras to determine distances between individuals. For a properly calibrated camera and a non-focal length, distances between individuals can be calculated using a single camera. Embodiments may use information from multiple cameras to determine locations of individuals and distances between individuals. In situations in which the detection module does not have enough information to compute the distance on its own, it may request information from other detection modules.

If the measured distances between individuals indicate that the individuals are not conforming to guidelines this information may be uploaded operation 244. In some embodiments, this information may be uploaded regardless of whether individuals are observing social distancing protocols. Although the illustrated example describes temperature measurement before social distancing measurements, the order of these operations may be reversed.

If (or regardless of whether) the measured distances between individuals indicate that the individuals are conforming to guidelines, the system continues processing information at operation 242 and the process continues at operation 240. At operation 240, if the local processor received a request from the server or a peer device to upload data, the system uploads that data.

If any of the trigger conditions are met (e.g., operations 236, 238 and 240, in any order), as noted above appropriate data is uploaded for analysis. In various embodiments, the system can be configured to collect and upload a window of data from the sensors using the 5G hotspot or other communications interface. The window of data may include, for example, +/−X seconds (or other interval) of data surrounding the trigger so that sufficient data is available for analysis. For example, the system may be configured to upload +/−5, 10, 15, 20, 25, 30, 31, 40, 45, 50, 55, 60 seconds of data or other amount of data as may be specified. In some embodiments, the system may use different criteria for the amount of time prior to the detection then the amount of time post detection. The system may also be configured to continue to send data as long as a symptomatic individual is within the field of view. For example, the detection module may continue to capture, store and forward data for as long as a person or persons exhibiting and above-threshold temperature condition are within the field of view of the detection module.

The cloud server or other central processing entity aggregates the data from the various sensors and devices in the various detection modules and may generate final results and alerts. The central processing entity can analyze all data clips, using timestamps for appropriate temporal overlap, and temperature or other sensor information to determine the situation among detected individuals. The system can determine whether one or more individuals exhibits any symptoms and whether social distancing protocols are being followed. The system can further evaluate data from other cameras to fill in image and temperature information corresponding to any occlusions as well as to track locations and whereabouts of individuals in other locations. Information collected from the detection modules 110 can be time stamped for synchronization purposes. The information can be synchronized at the edge or at the central processing entity.

The central processing entity can be configured to control the detection modules, which may include overriding certain features to augment data capture. For example, if a detection module is not triggered (e.g., it did not detect an individual due to an occlusion), but another detection module in the same location is triggered, the central processing entity can command the other detection module to trigger so that it can receive a complete picture of the subject scene. In embodiments, the other detection module at the same location can initiate the override and trigger the first detection module to also capture data of the scene.

As noted above, the central processing entity can trigger alerts, which may include alerts, data or other information. For example, where an individual is identified as exhibiting a symptom (e.g., high temperature) and individuals identity is known, the system may notify that individual that they exhibit this symptom. Alternatively, alerts can be sent to the individual updating them of status even if they are asymptomatic. Where the individual is not conforming to contemporary social distancing protocols, alerts can be sent to inform the individual of this. Alternatively, where the individual is conforming, alerts can be sent thanking or congratulating the individual for their behavior. Alerts can also or alternatively be sent to healthcare workers, administrative agencies, enforcement officials, or other authorities or their representatives for tracking, informational and other purposes. As another example, if an individual is exhibiting symptoms and is not social distancing, other potentially affected individuals can be warned.

The system may also be configured to stream real-time results to a display, which may include a touchscreen display, that can display alerts of possible social distancing breaches or high-temperature individuals in an area under observation to enable further action by authorities. Officials or other monitors may receive information on their computer screens or portable devices to know whether there is a situation within their purview.

The system may be configured to create an updated database for contact tracing. Information regarding symptomatic individuals can be gathered such as for contact tracing purposes, and may include individual identification (which might not include personal identification), locations visited, persons contacted, persons contacted in violation of social distancing protocols, and other information. The information items can be time stamped. The database can be queried to determine whether an infected individual came into contact with other individuals and at which locations and times the contact took place. Contacted individuals and visited locations can be notified so that they can take appropriate steps in view of the contact with a potentially infected individual. The contact tracing may be visualized using the system database and a knowledge graph.

Figure 3:
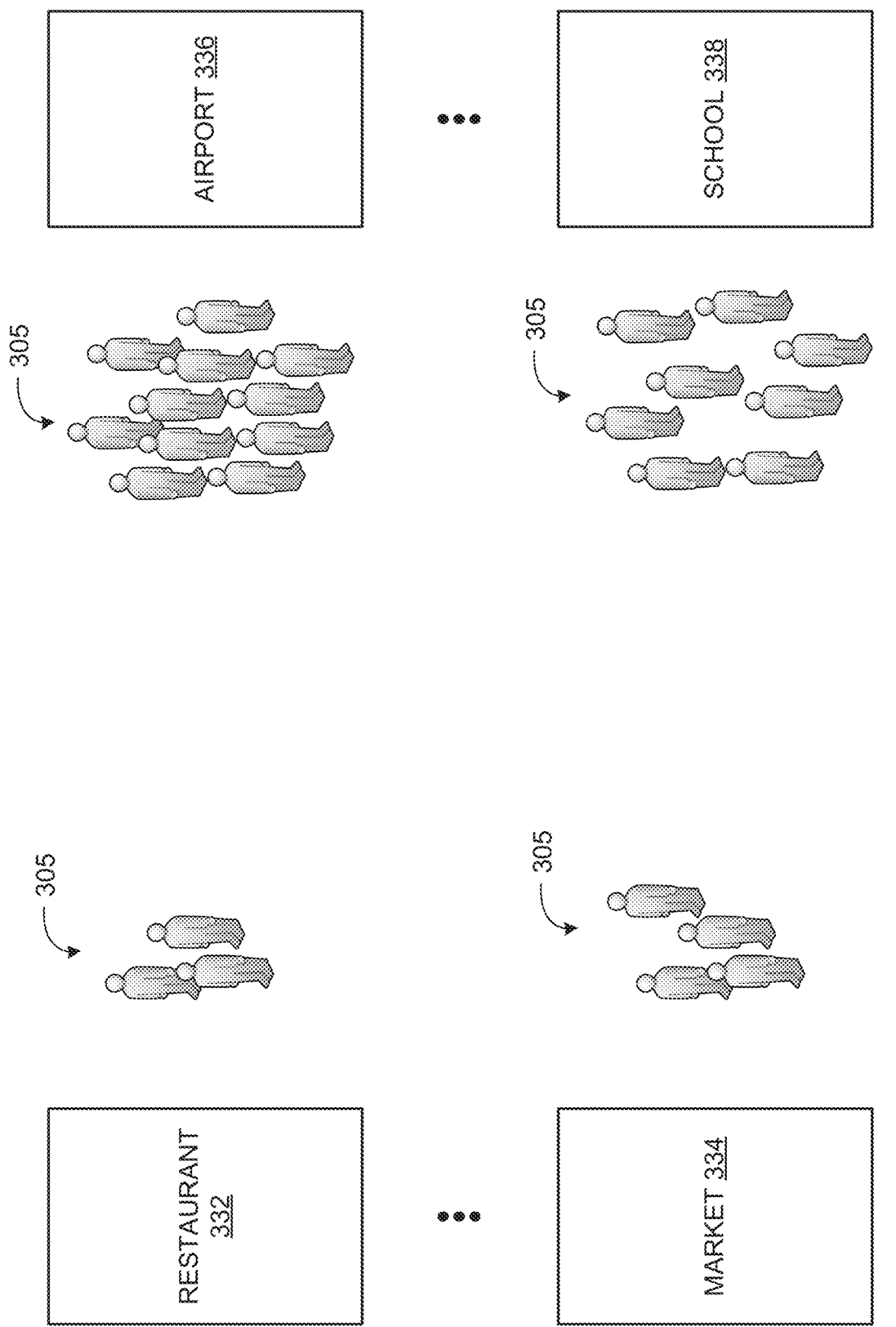
FIG. 3 illustrates an example environment with which embodiments of the systems and methods disclosed herein may be implemented.

FIG. 3 illustrates an example environment with which embodiments of the systems and methods disclosed herein may be implemented. The example of FIG. 1 illustrated two detection modules 110, 120 configured to monitor a location. The system may be deployed to include monitoring of multiple different locations by providing detection modules at these different locations. The information from the detection modules at multiple different locations can be synchronized to provide a more complete picture for contact tracing purposes. This information can also be combined with information from other sensors at various locations to further augment the data set. For example, security camera footage can be used in conjunction with image and other data from detection modules to provide a more complete picture of an individual's whereabouts and contacts.

The detection modules in this and other embodiments can be mounted in fixed positions such that they provide static or stationary monitoring of the monitored environment. For example, they can be mounted on fixed walls or ceilings, on columns or pillars, on bulkheads, or other fixed locations to provide monitoring. In other embodiments, all or part of the detection modules can be mounted on a movable rig, vehicle, drone, or other mobile platform so that the area being monitored and captured by the system can be dynamically defined. For example, mobile detection modules can be located and set up by personnel in desired locations, and relocated to another position as desired. As another example, detection modules can be configured to move about a larger area to capture a broader environment. Further to this example, detection modules can be mounted on a moving platform so they can be moved about and airport, stadium, theater, shopping center or other large facility; or moved about a park, town, city or other locality. Because camera calibration can be dynamic due to fiducial markers on each unit, movement or relocation in this manner can be accommodated because recalibration can be performed quickly using these markers. GPS units or other position determination systems can be utilized to capture the location of the units so that location information can be provided along with captured data. This can be useful for contact or other tracing, for example, in fixed or mobile configurations.

This example includes four locations, although other quantities of locations can be monitored. This example includes a restaurant 332, a market 334, and airport 336, and a school 338. Detection modules (e.g., detection modules 110, 120) can be provided at these locations to monitor the scene and gather pertinent information about individuals 305 at these locations. Accordingly, through the integration of information from a plurality of locations, more detail information about an individual, especially a symptomatic individual, can be obtained and used for purposes including contact tracing purposes.

Figure 4:
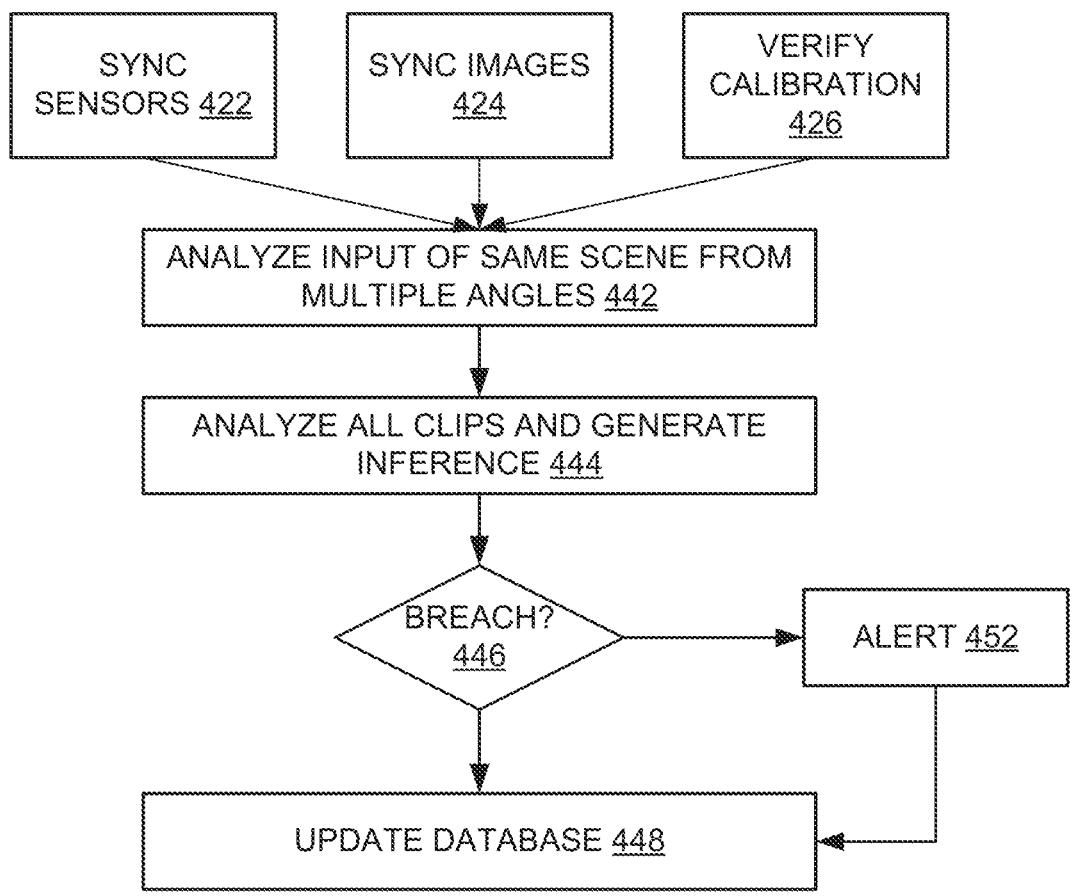
FIG. 4 illustrates an example process for data analysis at a central processing facility.

FIG. 4 illustrates an example process for data analysis at a central processing facility (e.g., a cloud server or other server) in accordance with embodiments. With reference now to FIG. 4, the central processing facility receives information from a plurality of detection modules. The detection modules can be located at the same location, or the information can come from detection modules at a plurality of different locations. As illustrated operations 422, 424 and 426 the system synchronizes the information received and verifies calibration. For example, the system synchronizes sensors and images (operations 422, 424), which may be accomplished using timestamps from the various data collection instruments. At 426, the system can also verify the calibration of the cameras, which may be based on information provided from the detection modules. The system can verify the last date/time of calibration and request the calibration refresh if the calibration information as stale or otherwise suspect.

Operation 442, with the information synchronized the system can analyze the information to determine the situation. For example, the system can analyze information of the same scene captured from different detection modules at that scene. This can provide information from different angles or perspectives because the detection modules may be mounted at different locations surrounding the scene. As noted above, information from multiple angles can be used to account for occlusions as well as provide greater accuracy for distance measurement or position determinations.

Operation 444, the system analyzes all of the data and generate an inference. The system can analyze image data to determine locations, positions and social distancing. The system can also analyze temperature data to determine whether individuals are exhibiting a symptom. Based on the analysis, at operation 446 the system determines whether a breach has occurred. In this context, a breach may refer to a breach of social distancing protocols and it may refer to a temperature above a determine threshold.

If a breach is detected, at operation 452 the system can send the appropriate alerts. As noted above, alerts can be messages or other information sent to the involved in individuals, officials, authorities or other personnel or instrumentalities. At operation 448, the system can update the database based on the information received in the analysis performed.

Figure 5:
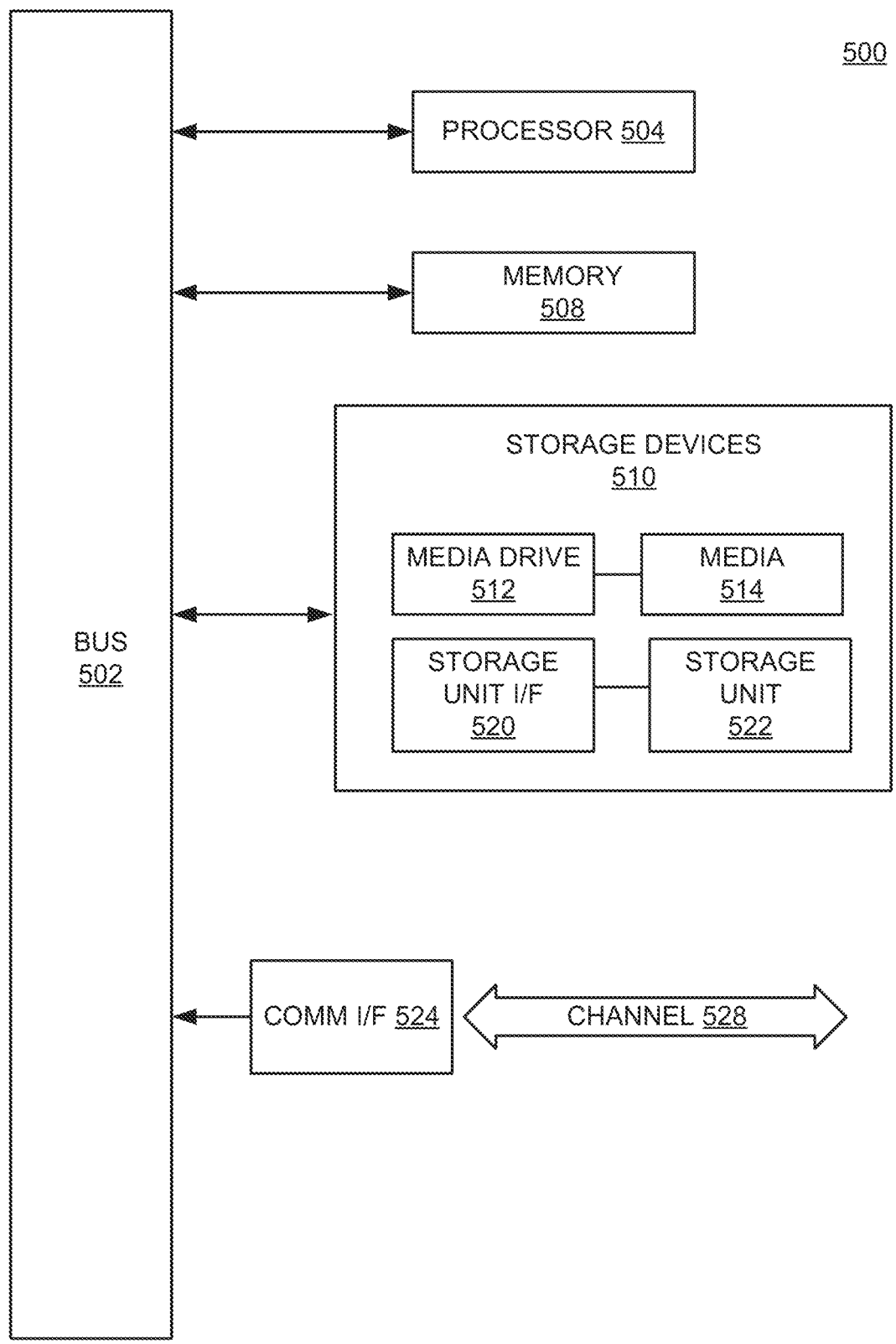
FIG. 5 illustrates an example computing module that may be used in implementing various features of embodiments of the disclosed technology.

As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared circuits in various combinations and permutations. Even though various features or elements of functionality may be individually described or claimed as separate circuits, one of ordinary skill in the art will understand that these features and functionality can be shared among one or more common circuits, and such description shall not require or imply that separate circuits are required to implement such features or functionality.

Where modules are implemented in whole or in part using software, in one embodiment, these software elements can be implemented to operate with a computing or processing system capable of carrying out the functionality described with respect thereto. One such example computing system is shown in FIG. 5. Various embodiments are described in terms of this example-computing system 600. After reading this description, it will become apparent to a person skilled in the relevant art how to implement the technology using other computing systems or architectures.

Referring now to FIG. 5, computing system 500 may represent, for example, computing or processing capabilities found within desktop, laptop and notebook computers; hand-held computing devices (smart phones, cell phones, palmtops, tablets, etc.); mainframes, supercomputers, workstations or servers; or any other type of special-purpose or general-purpose computing devices as may be desirable or appropriate for a given application or environment. Computing system 500 might also represent computing capabilities embedded within or otherwise available to a given device. For example, a computing system might be found in other electronic devices such as, for example, digital cameras, navigation systems, cellular telephones, portable computing devices, modems, routers, WAPs, terminals and other electronic devices that might include some form of processing capability.

Computing system 500 might include, for example, one or more processors, controllers, control modules, or other processing devices, such as a processor 504. Processor 504 might be implemented using a general-purpose or special-purpose processing engine such as, for example, a microprocessor (whether single-, dual- or multi-core processor), signal processor, graphics processor (e.g., GPU) controller, or other control logic. In the illustrated example, processor 504 is connected to a bus 502, although any communication medium can be used to facilitate interaction with other components of computing system 500 or to communicate externally.

Computing system 500 might also include one or more memory modules, simply referred to herein as main memory 508. For example, in some embodiments random access memory (RAM) or other dynamic memory, might be used for storing information and instructions to be executed by processor 504. Main memory 508 might also be used for storing temporary variables or other intermediate information during execution of instructions to be executed by processor 504. Computing system 500 might likewise include a read only memory ("ROM") or other static storage device coupled to bus 502 for storing static information and instructions for processor 504.

The computing system 500 might also include one or more various forms of information storage mechanism 510, which might include, for example, a media drive 512 and a storage unit interface 520. The media drive 512 might include a drive or other mechanism to support fixed or removable storage media 514. For example, a hard disk drive, a floppy disk drive, a magnetic tape drive, an optical disk drive, a CD or DVD drive (R or RW), a flash drive, or other removable or fixed media drive might be provided. Accordingly, storage media 514 might include, for example, a hard disk, a floppy disk, magnetic tape, cartridge, optical disk, a CD or DVD, or other fixed or removable medium that is read by, written to or accessed by media drive 512. As these examples illustrate, the storage media 514 can include a computer usable storage medium having stored therein computer software or data.

In alternative embodiments, information storage mechanism 510 might include other similar instrumentalities for allowing computer programs or other instructions or data to be loaded into computing system 500. Such instrumentalities might include, for example, a fixed or removable storage unit 522 and an interface 520. Examples of such storage units 522 and interfaces 520 can include a program cartridge and cartridge interface, a removable memory (for example, a flash memory or other removable memory module) and memory slot, a flash drive and associated slot (for example, a USB drive), a PCMCIA slot and card, and other fixed or removable storage units 522 and interfaces 520 that allow software and data to be transferred from the storage unit 522 to computing system 500.

Computing system 500 might also include a communications interface 524. Communications interface 524 might be used to allow software and data to be transferred between computing system 500 and external devices. Examples of communications interface 524 might include a modem or softmodem, a network interface (such as an Ethernet, network interface card, WiMedia, IEEE 802.XX, Bluetooth® or other interface), a communications port (such as for example, a USB port, IR port, RS232 port, or other port), or other communications interface. Software and data transferred via communications interface 524 might typically be carried on signals, which can be electronic, electromagnetic (which includes optical) or other signals capable of being exchanged by a given communications interface 524. These signals might be provided to communications interface 524 via a channel 528. This channel 528 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 508, storage unit 522, media 514, and channel 528. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing system 500 to perform features or functions of the disclosed technology as discussed herein.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various example embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described example embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of example block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:
1. A system, comprising:
a first monitoring device positioned at a first location to monitor a monitored environment; and
a second monitoring device positioned at a second location to monitor the monitored environment, wherein the first and second monitoring devices calibrate each other based on respective fiducial markers;
wherein the first and second monitoring devices each comprise a processor and a memory coupled to the processor, the memory storing a plurality of instructions, which when executed by the processor, cause the processor to perform the operations of:
detecting presence of an individual in the monitored environment;

determining whether a condition of interest of the individual exceeds a determined threshold; and based on the condition of interest of the individual exceeding the determined threshold, transmitting the condition of interest to a remote server to determine at least one of a social distancing breach and an identification of another person whom the individual contacted.

2. The system of claim 1, further comprising a communication interface to provide communication between the first and second monitoring device and the remote server.

3. The system of claim 2, wherein the communication interface comprises a 5G communication interface.

4. The system of claim 1, wherein the first and second monitoring devices each comprise a plurality of cameras, wherein the plurality of cameras capture images of individuals, and the captured images are used to determine locations of the individuals in the monitored environment, and further wherein the determined locations of individuals are used to determine whether the individuals are following determined social distance protocols.

5. The system of claim 4, wherein the first and second monitoring devices each further comprise a thermal sensor to detect information indicative of a temperature of individuals in the monitored environment.

6. The system of claim 5, wherein the condition of interest of the individual comprises a temperature of the individual, and wherein the operations further comprise correlating temperature information collected by the thermal sensor with an individual detected in the monitoring environment to determine whether temperature information associated with that individual exceeds a threshold temperature.

7. The system of claim 1, wherein the operations performed by the processor further comprise identifying the individual and tracking the individual as the individual moves through the monitored environment.

8. The system of claim 7, wherein tracking the individual further comprises identifying the individual prior to the individual moving behind an occlusion and re-identifying the individual when the individual emerges from behind the occlusion.

9. The system of claim 1, wherein the operations performed by the processor of the second monitoring device further comprise, based on the second monitoring device detecting an individual in the monitoring environment, the second monitoring device instructing the first monitoring device to begin monitoring the monitored environment.

10. The system of claim 1, wherein the condition of interest comprises a distance between the individual and another individual in the environment, and wherein determining whether the condition of interest of the individual exceeds the threshold comprises determining whether the individual is closer in distance to the other individual by less than a threshold amount.

11. The system of claim 1, further comprising the remote server, wherein the remote server is communicatively coupled to the first and second monitoring devices, the remote server receiving data from the first or second monitoring devices, the data indicative of the condition of interest regarding the individual present in the monitored environment.

12. A system, comprising:
a server; and
a plurality of monitoring stations, each monitoring station located at a physical location separate from the other monitoring stations, each monitoring station comprising a first monitoring device to monitor the location and a second monitoring device positioned to monitor the location from a different perspective from the first monitoring device;

wherein the first and second monitoring devices each comprise:
a pair of cameras to capture images of the location;
a thermal sensor to capture temperature information of individuals in the location;
a processor; and
a memory coupled to the processor, the memory storing a plurality of instructions, which when executed by the processor, cause the processor to perform the operations of:
detecting a presence of an individual in a monitored environment;
correlating temperature information with image information to determine a temperature of the individual in the monitored environment;
determining whether the temperature of the individual exceeds a determined threshold; and
based on the temperature of the individual exceeding the determined threshold, transmitting the information to a remote server to determine, based on information from other monitoring stations, other locations visited by the individual and other individuals contacted by the individual.

13. The system of claim 12, wherein the server is configured to receive time stamped information from the plurality of monitoring stations relating to the individual in a plurality of the monitored environments, the information including temperature and location of the individual, and the server is configured to analyze image information of the monitored environment from multiple angles to generate an inference regarding social distancing of the individual in the plurality of monitored environments.

14. The system of claim 13, wherein the server is further configured to determine whether the individual made contact with other individuals in any of the plurality of monitored environments without following social distancing protocols.

15. The system of claim 14, wherein the server is further configured to identify another individual with whom the individual made contact without following social distance protocols and to generate an alert to the other individual informing the other individual of the contact.

16. The system of claim 14, wherein the server is further configured to identify physical locations visited by the individual and to generate an alert to the identified physical locations or to other individuals who also visited the identified physical locations.

17. The system of claim 12, wherein the operations performed by the processor further comprise identifying the individual and tracking the individual as the individual moves through the monitored environment.

18. The system of claim 17, wherein tracking the individual further comprises identifying the individual prior to the individual moving behind an occlusion and re-identifying the individual when the individual emerges from behind the occlusion.

19. The system of claim 12, wherein the operations performed by the processor of the second monitoring device further comprise, based on the second monitoring device detecting an individual in the monitoring environment, the second monitoring device instructing the first monitoring device to begin monitoring the monitored environment.

* * * * *